United States Patent [19]

Seiler

[11] Patent Number: 5,334,190
[45] Date of Patent: Aug. 2, 1994

[54] LASER THERMOKERATOPLASTY METHODS AND APPARATUS

[75] Inventor: Theo Seiler, Zell, Fed. Rep. of Germany

[73] Assignee: Summit Technology, Inc., Waltham, Mass.

[21] Appl. No.: 883,055

[22] Filed: May 8, 1992

Related U.S. Application Data

[63] Continuation of Ser. No. 598,118, Oct. 16, 1990, abandoned.

[51] Int. Cl.$^5$ .............................................. A61N 5/06
[52] U.S. Cl. ........................................... 606/5; 606/3; 606/13; 606/16; 606/17; 607/88; 607/89
[58] Field of Search ....................................... 606/3-6, 606/13-19; 128/343, 347, 398, 898; 607/88, 89

[56] References Cited

U.S. PATENT DOCUMENTS

| | | | |
|---|---|---|---|
| 4,330,763 | 5/1982 | Esterowitz et al. | 372/41 |
| 4,381,007 | 4/1983 | Doss | 606/5 |
| 4,391,275 | 7/1983 | Fankhauser et al. | 606/6 |
| 4,461,294 | 7/1984 | Baron | 606/4 |
| 4,538,608 | 9/1985 | L'Esperance, Jr. | 606/4 |
| 4,558,698 | 12/1985 | O'Dell | 606/6 |
| 4,580,559 | 4/1986 | L'Esperance | 606/5 |
| 4,583,539 | 4/1986 | Karlin et al. | 606/4 |
| 4,729,373 | 3/1989 | Peyman | 606/15 |
| 4,917,084 | 4/1990 | Sinofsky | 606/18 |

FOREIGN PATENT DOCUMENTS

| | | |
|---|---|---|
| 0214712 | 5/1986 | European Pat. Off. |
| 9012618 | 11/1990 | PCT Int'l Appl. |
| 9100063 | 1/1991 | PCT Int'l Appl. |
| 822407A | 9/1979 | U.S.S.R. |
| 2228344 | 1/1986 | United Kingdom |
| 3518256 | 3/1987 | United Kingdom |
| 8906519 | 7/1989 | World Int. Prop. O. .............. 606/5 |

OTHER PUBLICATIONS

"A new cool lens capsulatomy laser" by Horn et al; Am Intra-ocular Implant Soc.; vol. 8, Fall 1982 pp. 337-342.

"A New Refractive Method for Laser Thermal Keratoplasty with the Co:MgF$_2$ Laser" by Horn et al Presented at the 2nd American-International Congress on Cataract IOL and Refractive Surgery, ASCRS Wash., D.C. Apr. 25, 1989.

"Infared Laser Surgery of the Cornea" by Stern et al; Ophthalmology vol. 95 No. 10 Oct. 1988; pp. 1434-1441.

Horn et al., *New refractive method for laser thermal keratoplasty with the Co:MgF$_2$ laser*, J. Cataract Refract Surg., vol. 16 (Sep. 1990), pp. 611-616.

Mainster et al. (1970) Applied Optics 9/3:655-667.

Kanoda Laser Correction of Hypermetropic Refraction.

Taboada (1990) Optics Letters 15:458-460.

Moulton (1985) IEEE Journal of Quantum Electronics QE-21:1582-1595.

Mainster (1979) Investigative Ophthalmology & Visual Science 18/4:416-420.

Doss et al. (1978) Los Alamos Scientific Laboratory Informal Report.

Rowsey et al. (1980) Contact & Intraocular Lens Medical Journal 6/1:1-12.

Gasset et al. (1975) American Journal of Ophthalmology 79/2:336-232.

*Primary Examiner*—David M. Shay
*Attorney, Agent, or Firm*—Thomas J. Engellenner

[57] ABSTRACT

Methods and apparatus for correction of optical defects in vision, employing an infrared radiation source and a focusing element, for changing the curvature of the eye by application of focused infrared radiation into the collagenous tissue of the cornea in a controlled manner.

15 Claims, 2 Drawing Sheets

LASER THERMOKERATOPLASTY METHODS AND APPARATUS

This application is a continuation of application Ser. No. 598,118, filed Oct. 16, 1990, now abandoned.

BACKGROUND OF THE INVENTION

The present invention relates to methods and apparatus for non-surgical alteration of corneal curvature in the human eye.

Refractive errors in the function of the eye are quite common in the human population. In fact, moderate levels of far-sightedness ("hyperopia"), near-sightedness ("myopia"), and astigmatism are so widespread as to be considered normal. Less common are the pathological cases which can be severe or degenerative in nature. While Telatively mild refractive errors often can be corrected by external lenses, larger and more complex refractive errors are more difficult and sometimes impossible to correct with external refraction alone.

In the field of surgery, a known technique for treatment of certain forms of refractive errors, such as acute myopia, hyperopia, and astigmatism is to surgically remove an anterior segment of the cornea down into the stroma, to reshape the removed segment as by surgical grinding in a frozen state, and to restore the reshaped segment into the eye. In this type of operation, known as keratoplasty, the eye heals by reformation of the outer epithelium layer over the reshaped stroma.

Alternatively, a layer of the cornea can be opened as a flap, an artificial or donor lenticular implant then inserted under the flap, and the flap sutured up again.

Such invasive corneal procedures are typically limited to treatment of severe conditions, and are generally viewed as a procedures of last resort because of the attendant surgical risks. Nonetheless, a substantial portion of the eye's refractive power is determined by the corneal curvature and reshaping the cornea has been the object of much research and experimental efforts as a means for correction of refractive errors.

Thermokeratoplasty, a class of procedures involving the application of heat to the cornea, has been proposed for hyperopic correction of optical defects. The collagen which forms the corneal stroma is known to shrink by about one third of its initial length when treated to a temperature between about 60°–70° C. This shrinkage appears to be permanent, with the potential of little or no lasting opacity of the treated site resulting from the treatment. Hence, various thermokeratoplasty techniques seek to exploit such collagen shrinkage profile, including inserting a nicrome wire into the cornea and heating the surrounding collagen tissue to a non-damaging temperature to cause permanent shrinkage of the collagen tissue. This shrinkage beneficially changes the curvature of the cornea. Other techniques include application of RF current or laser energy to effect permanent change in the corneal collagen.

A problem with heating of the eye lies in the possibility of damage to the epithelium and Bowman's membrane on the anterior side of the cornea, as well as Descemet's membrane and the endothelium on the corneal posterior, as heat energy is applied to develop a critical shrinkage temperature in the internal stromal collagen. It is therefore desirable to minimize the heating effect in these sensitive membranes, and particularly in the endothelium, while still obtaining the desired 60°–70° C. temperature range in the stroma. Thus, the treatment duration and other paremeters that affect the thermal dose to the cornea must be precisely controlled in any treatment delivery system.

It is therefore an object of the present invention to provide a non-surgical and non-damaging thermal treatment method and apparatus for the correction of the refractive power of the cornea.

It is another object of the present invention to provide a method and apparatus particularly useful for hyperopic and astigmatic correction by selectively applying heat to the cornea to induce volumetric coagulation in the corneal collagen and thereby steepen regions of the central cornea.

SUMMARY OF THE INVENTION

Methods and apparatus for correction of optical defects in vision are disclosed, employing an infrared radiation source and a focusing element, for changing the curvature of the eye by application of focused infrared radiation into the collagenous tissue of the cornea in a controlled manner.

In one aspect of the present invention, an apparatus for performing thermokeratoplasty includes a radiation source for delivery of infrared radiation into the cornea of an eye, and a focusing arrangement for focusing radiation from the source into the cornea in a controlled manner such that the focus of the radiation is limited to a predetermined depth, whereby the radiation effects heat-induced shrinkage of the collagenous tissue of the cornea and thereby changes the corneal curvature.

The radiation source can be laser or a non-coherent infrared radiation source, preferably operating at a wavelength ranging from about 1.8 micrometers to about 2.3 micrometers. The output can be pulsed or continuous wave ("CW"). Examples of laser radiation sources include Holmium:YAG lasers and $CoMgF_2$ lasers. Such laser sources can be configured to deliver radiation at a fixed wavelength or be tunable over at least a portion of the infrared spectrum.

The radiation source can be coupled to a handpiece which is utilized by the practitioner to create irradiation patterns or zones in the eye. The radiation source can be coupled to the handpiece by an optical fiber or other waveguide, and the handpiece can also include a focusing mechanism, which focuses the radiation into a cone-shaped beam and thereby defines a conical coagulation zone in the cornea. The focusing apparatus can be formed by refractive elements, such as lens, or reflective elements, such as mirrors, or combinations of such elements. Alternatively, the focusing apparatus can be incorporated into the waveguide, such as by the use of a tapered fiber terminus, which internally focuses the radiation into a cone. In any event, the focusing elements preferably focus the laser radiation to a depth of less than about 450 micrometers in the corneal tissue.

The apparatus can further include one or more interface-matching elements, disposed either between the fiber terminus and the focusing elements, or between the focusing elements and the surface of the cornea, or both. The interface-matching elements can have an index of refraction which provides a less abrupt transition between the different transmission media and thereby minimizes reflective or scattering losses. The interface-matching element can be a fluid medium or a graded optical element.

In one illustrated embodiment of the invention, the apparatus includes a laser infrared radiation source, a handpiece incorporating a focusing means, and a fiber optic cable which connects the laser to the handpiece. The focusing means is mounted on the handpiece and including a lens arrangement, from which a beam of laser radiation may be projected to a depth of about 300 to 450 micrometers into the cornea of the eye when the handpiece is brought into proximity with the corneal surface and the laser is activated.

In another aspect of the invention, a method for shrinking collagen tissue in an eye to correct refractive errors is disclosed which includes generating a beam of radiation in the infrared range, focusing the beam to a controlled focal depth and applying the focused radiation to the cornea of an eye such that the beam is focused into the cornea, causing the collagenous tissue in the focal region to shrink. Preferably, the beam is focused to a point about 300 to 450 micrometers in the eye.

BRIEF DESCRIPTION OF THE DRAWINGS

These and other features and advantages of the present invention will be more fully understood by reference to the following detailed description in conjunction with the attached drawing in which like reference numerals refer to like elements and in which.

DETAILED DESCRIPTION

Figure 1:
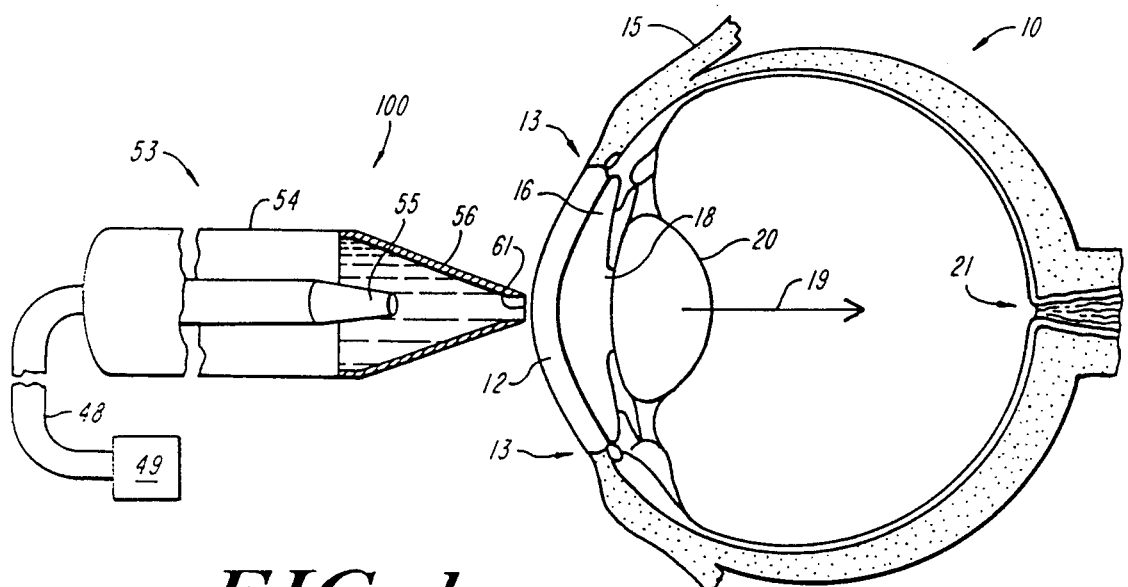
FIG. 1 is a schematic view of an embodiment of the present invention in cooperation with an eye shown in cross-section.
Figure 2:
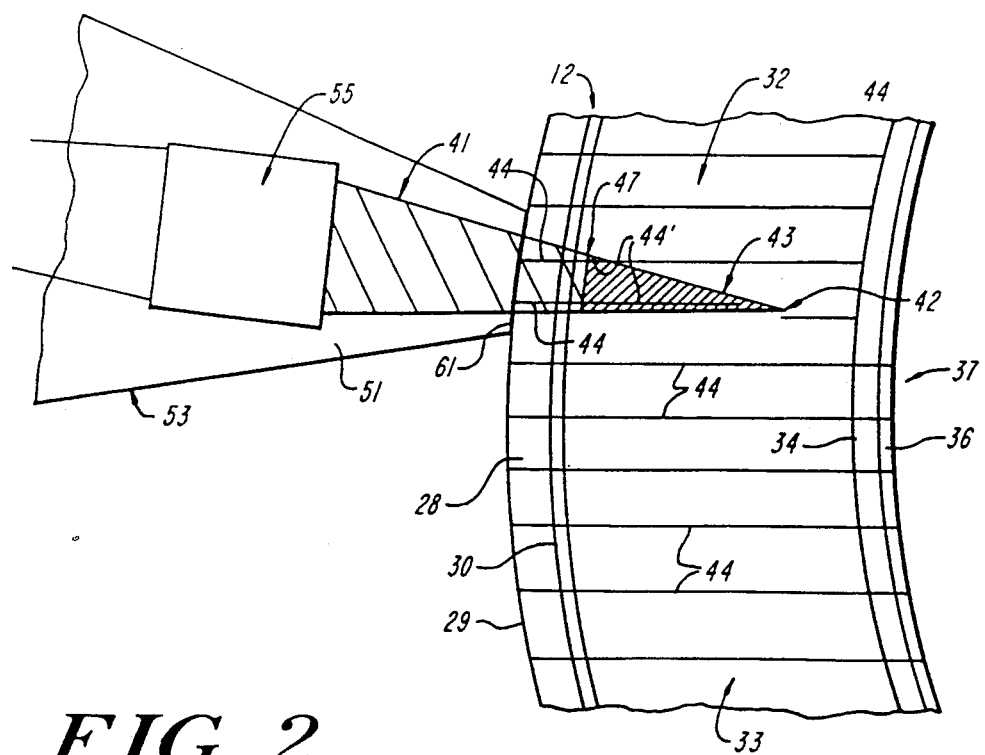
FIG. 2 is a more detailed view of another embodiment of the present invention operating upon an eye.

An embodiment of the present invention is shown in FIGS. 1 and 2 in cooperation with a human eye. A typical human eye 10 includes a cornea 12, iris 16, pupil 18, lens 20 and retina 21 at the back of the eye. These parts receive light rays 19 from the environment and convert the captured light rays 19 into electrical impulses for processing in the brain. The outer portion of eye 10, the sclera 15 (commonly referred to as the "whites" of the eye), is attached to and bounds the periphery 13 of the cornea. The typical radius of curvature of the outer surface of cornea 12 in the human eye is about 8 millimeters, which is smaller than the average radius of curvature of the sclera, thus giving the cornea its characteristic bulged-out contour, as shown. Cornea 12 is a layered structure the curvature of which provides a major portion of the refractive power of the eye.

As shown in more detail in FIG. 2, the cornea includes several layers: the anterior epithelium 28, Bowman's membrane 30, the relatively thick collagenous stroma 32, Descemet's membrane 34, and the posterior endothelium 36. The human corneal thickness, from the outer surface 29 of epithelium 28 to the outer surface 37 of endothelium 36, is typically about 450 micrometers. The cornea is formed having a multiplicity of collagen fibers 44 generally extending between the cornea anterior surface 29 and posterior surface 37.

In practice of the invention, selected portions of the collagen fibers are shrunk by application of a focused beam 41 of heat energy from a focusing system 55 of delivery device 53, forming a coagulation cone 43. The beam preferably generates a temperature of at least about 60° C. in the target area, so as to safely cause a volume coagulation of portions 44' of fibers 44. The coagulation cone 43 extends essentially from behind Bowman's membrane 30 at the anterior side 47 of cone 43 to region of the beam's focal point 42 within the stroma 32 and anterior to Descemet's membrane 34. The contracted fiber portions 44' cause a correlated contraction of the cornea, thus achieving a desired corrected index of refraction of the cornea.

Various corrective procedures can be accomplished by selective heating of the cornea and consequent selective shrinkage of the stromal collagen. In one technique, simple hyperopic corrections can be achieved by formation of a ring-shaped pattern of coagulation spots about the optical axis. Larger hyperopic corrections can be achieved by applying two or more concentric ring patterns. Astigmatic corrections can be achieved by applying a line of coagulation spots to induce steepening along a treatment axis. Corrections of myopia can be achieved by either central application of the focused energy beam or by the application of radial patterns. These techniques can also be practiced in combination to achieve an overall correction of multiple refractive errors.

Figure 4:
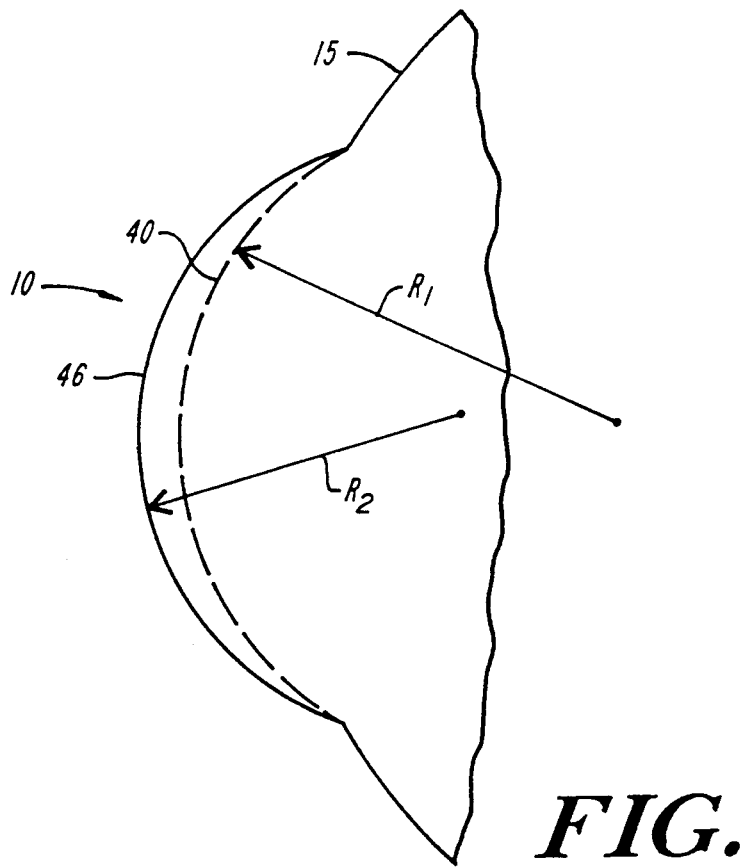
FIG. 4 shows changes in the cornea after treatment according to the invention.

The curvature of cornea 12 is shown in FIG. 4 before and after treatment in practice of the present invention to correct hyperopia. The pretreatment corneal curve 40 is shown in dotted outline having a first radius R1 and the post treatment corneal curve 46 is shown in solid outline having a lesser radius R2. The change from radius R1 to R2 correlates to a refractive correction which can be achieved by application of the techniques disclosed herein.

Careful application of heat energy is essential to avoid damaging the delicate layers and structures anterior or posterior of stroma 52. Nevertheless, enough heat must be applied to the stroma to effect permanent fiber shrinkage. Hence, the applied heat energy is preferably controlled to generate sufficient heat in the stroma at desired sites without generating damaging heat in surrounding tissues. A ring marker can be used to mark the cornea and to locate exposure sites on the ring circumference. A series of exposures are then made along the ring circumference. This creates a plurality of conical exposure sites within the cornea, with a consequent reformation of the cornea.

Apparatus 100 of the invention, shown in FIGS. 1 and 2, applies infrared radiation from a radiation source 49 (e.g., a Ho:YAG laser), guided by fiber 48 and via delivery device 53, to cornea 12. Delivery device 53 can include a handpiece 54 and a corneal contact adapter 56, with a focusing system 55 (e.g., a tapered optical waveguide as shown in FIG. 1 or equivalent) mounted in adapter 56 (or in handpiece 54) for focusing beam 41, delivered by fiber 48 from source 49, to focal point 42.

Figure 3:
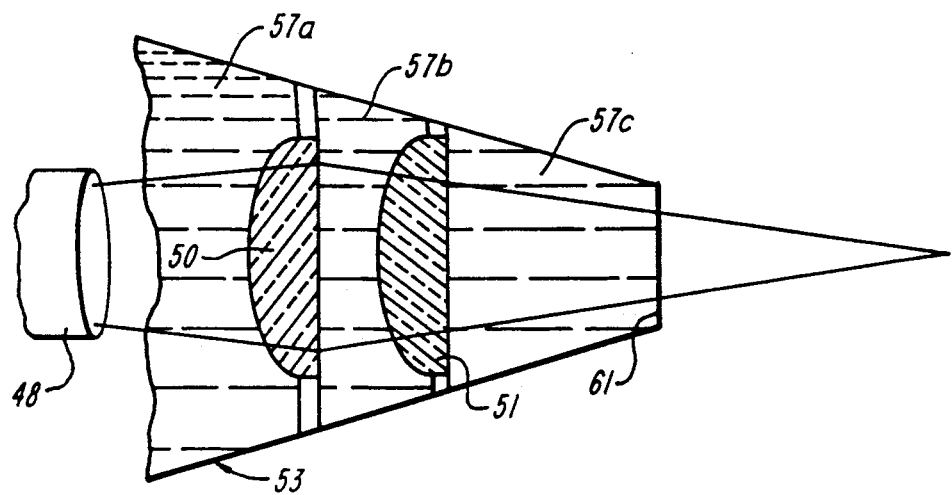
FIG. 3 is a more detailed schematic view of a focusing mechanism for use in the present invention.

Various focusing mechanisms can be used to implement focusing means 55. For example, in FIG. 3 a configuration of two lenses 50, 51 is shown. The first lens 50 collimates the output of fiber 48 and the second lens 51 focuses the beam. As shown, three separate chambers 57a, 57b, and 57c are filled with index matching fluid. The fluid in each chamber can be the same or different depending on the optic properties desired. Lenses 50, 51 can be plano-convex or otherwise fabricated as a convergent lens system to effect a conical exposure volume within the cornea. (It should be clear that various other optical focusing elements, including single lens systems, three or more lens arrangements, reflective elements, light pipes, Fresnel lenses, microlenslets, and graded refractive index lenses, can be employed to achieve similar conical exposure volumes within the cornea.)

Returning to FIG. 2, it can be seen that the focusing means 55 creates a shallow conical exposure region, i.e., a shallow cone 43 typically extending to a depth of about 300 to 400 micrometers into the cornea. Hence, the infrared energy of the radiation source will be focused slightly beyond the center of the stroma, at focal point 42, which isolates the heat damage to cone 43 away from the more sensitive anterior and posterior layers 28, 30, 34, 36. By means of this pattern control, a precise coagulation pattern (generally coincident with cone 43) can be obtained with the greatest heat intensity located around the mid-stroma 33. The coagulation of the treated stroma thus causes a local pinching effect on the cornea, with resulting optical correction. Furthermore, it has been observed that in this embodiment there is a very rapid decrease of the beam fluence beyond focal point 42, thus preventing damage to the highly sensitive endothelial layer.

The corneal contact adapter 56 can have a concave shaped receiver end 61 which facilitates applying delivery device 53 directly to the surface of the cornea, and therefore affords accurate presentation of the radiation beam to the eye. Contact adapter 56 can also be removably attached to handpiece 54 (such as by mechanical and/or frictional engagement) such that adapter 56 can be discarded (or sanitized) after use. This provides an added degree of safety and convenience in practice of the presently disclosed invention.

Contact adapter 56 can be filled with a fluid medium 57 having an index of refraction which provides a transition from fiber 48 to the cornea to be treated, so as to more accurately define the treatment zone in the eye. When a conical focusing element is used as the focusing element 55, as shown in FIG. 1, it can be bathed in fluid medium 57 (e.g., a saline or other solution) within adapter 56.

It will now be appreciated that as a result of the present invention, it is possible to recontour the corneal curvature by radially shrinking collagen fibers axially cooperating with the cornea surface. Volumetric coagulation is achieved without injuring the surface of the cornea or stroma. Furthermore, as a result of focusing the radiation beam, it is possible to obtain a nearly homogeneous coagulation pattern in cone 43 because the energy loss due to absorption is partially compensated by the focusing.

In one embodiment of the invention, a commercially available Ho:YAG laser (available, for example, from Schwarz Corporation, Orlando, Fla., USA) tuned to a wavelength of 2.06 micrometers, was employed with favorable results. The beam was guided by a quartz fiber (having a diameter of 400 micrometers) and was applied by a handpiece to the eye. A lens system (as specified above) was mounted in the handpiece to focus the beam about 300–400 micrometers in front of the handpiece into the eye with the handpiece in contact with the cornea. The energy output was maximally 35 mJ at a pulse repetition rate of 4 Hertz. Pulse duration was 200 microseconds. The output was adjusted from 10 to 35 mJ per pulse by changing the lamp voltage. Thirty pulses were applied to each coagulation site.

In one group of experiments performed on four blind eyes, two different pulse energies were studied: two eyes with 35 mJ per pulse, two eyes with 25 mJ per pulse. Coagulation sites were established using corneal marker rings having various diameters so that a series of exposures could be made on the circumference of a ring or rings, so to control the corneal shrinkage. The angle was carefully controlled to be wide so as to prevent damage to the endothelium. The treatment was under topical anesthesia. The post-operative medication consisted of Gentamicin ointment three to five times per day for three days. The patients have been followed with the following observations:

The principal change in corneal curvature, after eight coagulations and ring diameter of 6 millimeters, was a central steepening. The irregular corneal surface present during the first postoperative days disappeared after one week.

Refractive change (spherical equivalent) depended on pulse energy. There appears to be a therapeutic threshold at about 8 to 10 mJ per pulse and saturation limit at energies above 15 mJ per pulse. At about 15 mJ per pulse the effect is approximately linearly related with pulse energy.

The hyperopic correction is linearly related to the distance of the coagulations from the center of the cornea. However the hyperopic correction decreases linearly with increasing ring diameter in the range between 5 and 9 millimeters.

In the experiments, the coagulation stopped at about 15 micrometers from the Descemet's membrane, thus guaranteeing a safety zone between the coagulation and endothelium.

Intraoccular pressure dropped after surgery by 5 to 8 milligram Hg but returned to preoperative values after one week. Also, patients reported foreign body sensation during the first week. At postoperative day three, the epithelium was healed. No recurrent erosions were observed. The two patients treated with 35 mJ per pulse developed discrete flair in the anterior chamber which apparently resolved after about one week. The coagulation spots appeared to be homogeneously white during the first days. After one week there was an already detectable and later on more extensive transparent zone formed inside the coagulation cone. This opacification clears slowly.

Thus, it has been found that, in practice of the present invention, coagulation cones can be produced which end a sufficient distance (perhaps about 15 micrometers) from the endothelium. This is mainly due to focusing of the laser beam in conjunction with the strong absorption of infrared light by the corneal tissue, resulting in a penetration depth of about 300–400 micrometers. As stated above, the focused laser beam produces a cone-shaped coagulation. This leads to a more pronounced shrinkage of the collagen fibers in the anterior stroma compared to those of the posterior stroma resulting in a greater refractive effect and eventually increased stability, compared to exposure without such focused beams.

The need for caution in the use of the present invention is self-evident. If laser energy is too high, or improperly focused, damage to the endothelial layer is possible. This may be indicated by circumferential Descemet folds appearing immediately after treatment. To prevent the folds, and endothelial damage, the laser energy is diminished to a lower level and/or a shorter focal length lens system is employed, to assure that heat to the Descemet's membrane is maintained below approximately a safety threshold of 70° C.

The stability of the refractive outcome of the present invention is marked. After some fluctuation during the first week, with reduction of the induced astigmatism, the keratometer readings became stable for four months within the measurement errors. Essentially there was no reduction of the hyperopic effect of the treatment zone beyond about one month of recovery.

Generally, when a pulsed radiation source is employed, the laser energy delivered to the eye per pulse can range from about 5-50 mJ (preferably 15-35 mJ). As noted above, the radiation source can be either CW or pulsed. If the radiation source is pulsed, the pulse rate and duration should be chosen to deliver an effective amount of heat within the coagulation zone to induce collagen shrinkage. For example, the pulse rate can vary from about 0.1 to about 20 Hertz and the pulse duration can vary from about 700 nsec to 5 microsec. Typically, the total energy to the eye per spot will range from about 250 mJ to 1.2 J.

It will be understood that the above description pertains to only several embodiments of the present invention. That is, the description is provided by way of illustration and not by way of limitation. The invention, therefore, is to be defined according to the following claims.

What is claimed is:

1. An apparatus for performing thermokertoplasty comprising:
    a radiation source for delivery of infrared radiation in the wavelength range of about 1.8 microns to about 2.3 microns into a cornea of an eye, and
    focusing means for focusing radiation from the source into the cornea in a controlled manner such that the focusing means defines a coagulation cone with an apex at a depth less than about 450 microns in the cornea, whereby the radiation effects heat-induced shrinkage of the collagenous tissue of the cornea and thereby changes the corneal curvature.

2. The apparatus of claim 1 wherein the radiation source is pulsed laser having a repetition rate ranging from about 0.1 Hz to about 20 Hz.

3. The apparatus of claim 1 wherein the radiation source is a laser having an output wavelength in the range of about 1.8 micrometers to about 2.3 micrometers.

4. The apparatus of claim 1 wherein the radiation source is a laser having an output wavelength of about 2.06 micrometers.

5. The apparatus of claim 1 wherein the focusing means is integrated into a handpiece.

6. The apparatus of claim 1 wherein the focusing means includes a lens system.

7. The apparatus of claim 1 wherein the focusing system is a convergent waveguide.

8. The apparatus of claim 1 wherein the source includes a handpiece.

9. The apparatus of claim 1 further comprising an interface-matching means for minimizing transmission losses between the radiation source and the cornea.

10. The apparatus of claim 9 wherein the interface-matching means is a fluid medium.

11. The apparatus of claim 1 wherein the radiation source is a laser.

12. The apparatus of claim 11 wherein the laser is a Holmium:YAG laser.

13. The apparatus of claim 11 wherein the laser is a $CoMgF_2$ laser.

14. Apparatus for selective shrinking of collagen tissue in a cornea of an eye by focusing infrared radiation, the apparatus comprising:
    a source for generation of a beam of infrared radiation in the wavelength range of about 1.8 microns to about 2.3 microns,
    an optical fiber optically aligned with said source to transmit said radiation, and
    a handpiece optically aligned with said fiber to receive the radiation transmitted through the optical fiber, the handpiece including
        focusing means for focusing the radiation to a focal point in the cornea, and
        interface-matching means for minimizing transmission losses between the handpiece and the cornea,
    such that when the handpiece is placed in proximity to the cornea and the source is activated, a beam of radiation is delivered to a volume of the cornea as a coagulation cone with an apex no greater than about 450 micrometers in depth.

15. A method for shrinking collagenous tissue in a cornea of an eye comprising
    generating a beam of infrared radiation in the wavelength range of about 1.8 microns to about 2.3 microns,
    transmitting the beam to a focusing assembly having a distal end, which assembly is capable of focusing the beam in front of the distal end, and
    placing the distal end in proximity to a surface of the cornea of an eye such that the beam is focused into the cornea to define a coagulation cone with an apex at a depth of about 300 to 400 microns in the cornea, and a portion of the collagenous tissue of the cornea is subjected to nearly homogeneous coagulation and, thereby, induced to shrink.

* * * * *

UNITED STATES PATENT AND TRADEMARK OFFICE
CERTIFICATE OF CORRECTION

PATENT NO. : 5,334,190
DATED : August 2, 1994
INVENTOR(S) : Theo Seiler

It is certified that error appears in the above-indentified patent and that said Letters Patent is hereby corrected as shown below:

In Column 7, Line 23 in Claim 1:
   replace "1. An apparatus for performing thermokertoplasty" with --1. An apparatus for performing thermokeratoplasty--

In Column 7, Line 30 in Claim 1:
   replace "focusing means defines a coagulation cone with an" with --focussed radiation is compensated by corneal absorption to form a volumetric cone of heating in the cornea to an essentially homogeneous temperature within the cone and with an--

In Column 7, Line 34 in Claim 1:
   replace "and thereby changes the corneal curvature." with --to thereby change the corneal curvature--

UNITED STATES PATENT AND TRADEMARK OFFICE
CERTIFICATE OF CORRECTION

PATENT NO. : 5,334,190
DATED : August 2, 1994
INVENTOR(S) : Theo Seiler

It is certified that error appears in the above-indentified patent and that said Letters Patent is hereby corrected as shown below:

In Column 8, Line 32-33 in Claim 14:
replace "radiation is delivered to a volume of the cornea as a coagulation cone with an apex no greater than" with --radiation is delivered to the cornea and absorbed therein to form a volumetric cone of heating in the cornea to an essentially homogeneous temperature with an apex no greater than--

In Column 8, Line 44-45 in Claim 15:
replace "cornea of an eye such that the beam is focused into the cornea to define a coagulation cone with an" with --cornea of an eye such that the beam is focused and absorbed within the cornea to define a volumetric cone of heating in the cornea to an essentially homogeneous temperature with an--

UNITED STATES PATENT AND TRADEMARK OFFICE
CERTIFICATE OF CORRECTION

PATENT NO. : 5,334,190
DATED : August 2, 1994
INVENTOR(S) : Theo Seiler

It is certified that error appears in the above-indentified patent and that said Letters Patent is hereby corrected as shown below:

In Column 8, Line 48 in Claim 15:
   replace "the cornea is subjected to nearly homogeneous" with --the cornea is subjected to--

Signed and Sealed this

Twenty-seventh Day of December, 1994

Attest:

BRUCE LEHMAN

Attesting Officer     Commissioner of Patents and Trademarks